United States Patent
Rattner et al.

(10) Patent No.: US 6,585,731 B1
(45) Date of Patent: Jul. 1, 2003

(54) MEDICAL-TECHNICAL SYSTEM WORKSTATION

(75) Inventors: Manfred Rattner, Grossenseebach (DE); Bernd Malter, Effeltrich (DE); Thomas Reichert, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/252,919

(22) Filed: Feb. 19, 1999

(30) Foreign Application Priority Data

Feb. 20, 1998 (DE) ......................... 198 07 242

(51) Int. Cl.[7] ................................. A61N 1/00
(52) U.S. Cl. ............................. 606/34; 607/1
(58) Field of Search ................ 606/32, 34, 37, 606/35, 39, 45; 607/1, 2, 102, 109, 101; 52/36.1, 36.2, 36.4, 39, 40

(56) References Cited

U.S. PATENT DOCUMENTS 5,409,002 A * 4/1995 Pell ........................... 600/407

FOREIGN PATENT DOCUMENTS

| DE | 92 18 373 | 3/1994 | |
| FR | 1317060 | * 12/1962 | .................. 606/32 |

* cited by examiner

Primary Examiner—Jeffrey R. Jastrzab
(74) Attorney, Agent, or Firm—Schiff Hardin & Waite

(57) ABSTRACT

A medical-technical system workstation for open or minimally invasive surgery has a patient support mechanism and at least one medical device with at least one applicator connected to the medical device. The medical device is attached to the ceiling of a room containing the workstation, or in or at the patient support mechanism or in or at a unit that can be placed at the patient support mechanism.

5 Claims, 6 Drawing Sheets

MEDICAL-TECHNICAL SYSTEM WORKSTATION

BACKGROUND OF THE INVENTION

1. Field of the Invention

The present invention is directed to a medical-technical system workstation for open or minimally invasive surgery of the type having a patient support mechanism and at least one medical device from the group of cold light source, RF device, video device or ultrasound device, with at least one applicator connected to the medical device.

2. Description of the Prior Art

As a rule, system workstations of the above general type have a device cabinet for the acceptance of medical devices of the system workstation that is arranged at some distance from the patient support mechanism in order to give an operating team adequate movement and action space around the patient support mechanism for conducting surgical procedures. The medical devices of the system workstation are provided with applicators that, for example, are placed on a presentation unit arranged at the patient support mechanism and are available to a surgeon at the system workstation. The applicators are connected via connecting lines to the medical devices integrated in the device cabinet. It has proven to be a disadvantage that the usually long lengths of the connecting lines between the medical devices and the appertaining applicators, particularly between an RF device and an RF applicator, cold light source and cold light, video device and image pick-up unit and ultrasound device and ultrasound applicator produce problems with respect to line losses, noise levels and impedance discontinuities.

A system workstation disclosed in German Utility Model 92 18 373 wherein an RF device, a cold light source and a video device are arranged in a mobile device cabinet placed at the patient support mechanism in fact has short lines from devices to the appertaining applicators; the device cabinet, however, represents an impediment for the operating team working at the patient support mechanism during a surgical procedure.

SUMMARY OF THE INVENTION

It is an object of the present invention to provide a medical-technical system workstation of the type initially described wherein the connecting lines between the medical devices of the system workstation and the appertaining applicators are optimally short and the arrangement of the medical devices of the system workstation does not represent any impediment for the personnel working at the system workstation.

According to the invention, this object is achieved in a medical-technical system workstation for open or minimally invasive surgery having a patient support mechanism and at least one medical device from the group of cold light source RF device, video device or ultrasound device, with at least one applicator connected to the medical device, and in the medical device is attached at the ceiling of a room containing the medical workstation, or in or at the patient support mechanism, or in or at a unit from the group anesthesia unit instrumentation table, and operating seat placed at the patient support mechanism. Inventively, devices of a system workstation such as cold light sources, RF devices, video devices or ultrasound devices, wherein problems with respect to line losses, noise level and impedance discontinuities can arise due to long lines between the devices and the appertaining applicators of the devices, are placed optimally close to the operating site, i.e. the patient support mechanism, so that the connecting lines between the devices and the appertaining applicators employed given surgical interventions are short. The problem of a lack of space around the patient support mechanism for the operating team composed of surgeons, anesthesiologists, operating room nurses and operating room attendance is taken into consideration by the invention with equipment arranged at the patient bearing mechanism, by attaching the medical device to the ceiling of the room containing the workstation, or in or at functional equipment of the system workstation that are already placed in the immediate proximity of the patient support mechanism for conducting a medical procedure. Such function equipment can be the patient support mechanism itself as well as anesthesia equipment, instrumentation tables or operating seats for the operating team. An advantage of the present invention is thus that no additional equipment such as, for example, a device cabinet for the acceptance of RF devices, cold light sources, video devices or ultrasound devices need be placed at the patient support mechanism that would restrict the movement and action space of the operating team. The various devices need not all be attached to a single unit but can also be attached to different units.

In one version of the invention the applicator is a cold light connected to the cold light source or a high-frequency scalpel connected to the RF device or a camera connected to the video device or an ultrasound applicator provided for diagnostic and/or therapeutic purposes that is connected to the ultrasound device. The cold light, the high-frequency scalpel, the camera as well as the ultrasound applicator are thus inventively connected via short lines to the appertaining devices, namely the cold light source, the RF devices, the video device and the ultrasound device, so that the risk of problems in the signal transmission as a consequence of line losses, noise levels or impedance discontinuities is reduced.

In another embodiment of the invention the workstation includes a connection unit having connectors for the applicators of the medical devices, with the medical devices being connected to the connection unit. The connection unit can have a number of connectors for cold lights, high-frequency applicators, cameras or ultrasound applicators that can be connected to the connectors with connecting lines. According to another version of the invention, the connection unit is arranged at an adjustable holder, so that the connection unit can be selectively aligned relative to the operating site, for example as desired by the operating surgeon. It is an advantageous that the path of the cables of the connecting lines of the applicators from the connection unit to the applicators is practically parallel, enabling a simple cable management.

In a further version of the invention the connection unit is a component of an operating lamp of the system workstation. In this way, the connection unit, given a surgical procedure, can be adjusted relative to the operating site in only one manipulation together with the operating lamp achieving, a synergistic effect.

DESCRIPTION OF THE PREFERRED EMBODIMENTS

Figure 1:
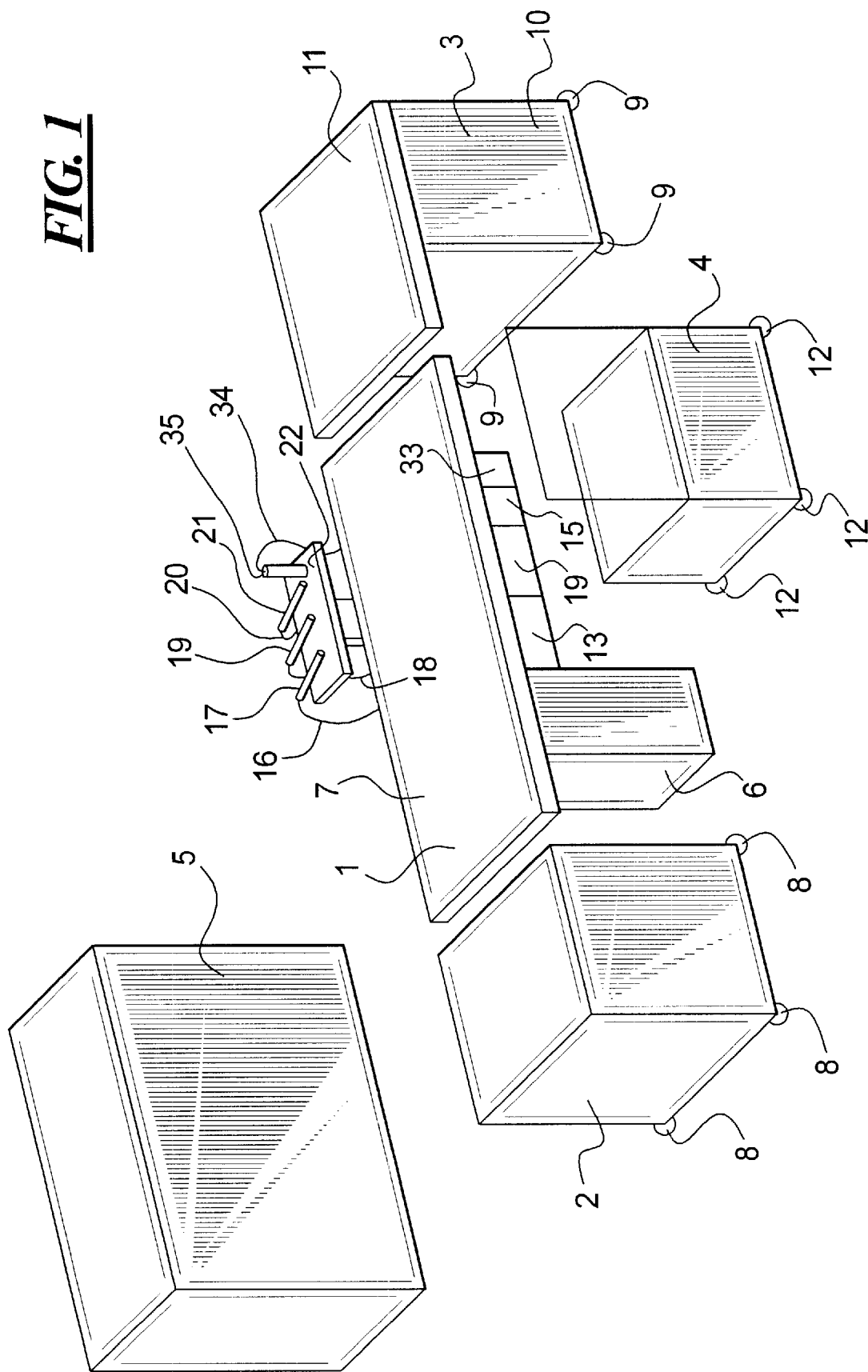
FIG. 1 shows an inventive system workstation wherein a cold light source, a RF device, a video device, and an ultrasound device are attached to the patient support table.

FIG. 1 shows an inventive medical-technical system workstation for open or minimally invasive surgery. The system workstation includes a patient support mechanism in the form of a patient support table 1, an anesthesia tower 2, an instrumentation table 3, an operating seat 4 and a device cabinet 5.

The patient support table 1 has a lifting column 6 and a patient support plate 7 arranged at the lifting column 6. The lifting column 6 is vertically adjustable in a known way.

The anesthesia tower 2 is provided with wheels 8 for free positioning relative to the patient support table 1 and, in a way that is known and not shown in detail, contains devices that serve for anesthetizing a patient, de-anesthetizing a patient and for monitoring the life functions of an anesthetized patient on the patient support plate 7 during a surgical intervention. The patient is not shown in the Figures.

The instrumentation table 3 includes a cart 10 provided with wheels 9 and a table top 11 arranged on the cart 10 for the acceptance of medical instruments, applicators and operation material.

The operating seat 4 likewise has wheels 12 and is provided, for example, for allowing a surgeon working at the system workstation to be seated, in order to avoid long, strenuous standing during lengthy operations.

The device cabinet 5 of the system workstation, which is arranged at a distance from the patient support table 1 so that it does not impede the motion and action space of an operating team composed of surgeons, anesthesiologists, operating room nurses and operating room attendants during surgical procedures, accepts devices and controls of medical devices of the system workstation in a known way that is not shown in detail. Included among these are, for example, a rinse/suction pump control, an insufflator, etc. The devices and controls are connected (in a way not shown in detail) via connecting lines to applicators (not shown in the Figures) belonging to the devices, for example a rinse/suction applicator, an insufflation applicator, etc. The applicators are arranged at the patient support table 1, for example on the table top 11 of the instrumentation table 13, within the reach of a surgeon working at the system workstation or within the reach of an assisting person.

In the exemplary embodiment, the system workstation also has a cold light source 13, an RF device 14, a video device and an ultrasound device 33. In the exemplary embodiment, the ultrasound device 33 is an ultrasound device for diagnostic purposes, however, the ultrasound device could also be an ultrasound device provided for therapeutic purposes, for example a HIFU source (high focussed ultrasound). The cold light source 13 is connected via a connecting line 16 to a cold light 17; the RF device 14 is connected via a connecting to a high-frequency scalpel 19; the video device 15 is connected via a connecting line 20 to an endoscope camera 21; and the ultrasound device 33 is connected via a connecting line 34 to an ultrasound applicator 35. In the exemplary embodiment, the cold light 17, the high-frequency scalpel 19, the endoscope camera 21 and the ultrasound applicator 35 are arranged on a presentation unit 22 that is displaceably arranged at the patient support plate 7 of the patient support table 1, for example on rails of the patient support plate 7. The cold light source 13, the RF device 14, the video device 15 and the ultrasound device 33 are attached such to the patient support plate 7 of the patient support table 1 that the connecting lines 16, 18, 20, 34 between the cold light source 13 and the cold light 17, between the RF device and the high-frequency scalpel 19, between the video device 15 and the endoscope camera 21 and between the ultrasound device 33 and the ultrasound applicator 35 are short. In this way, problems occurring specifically given these device groups in the signal transmission between the devices and the appertaining applicators in the form of line losses, noise signals and impedance discontinuities are avoided.

The cold light source 13, the RF device 14, the video device 15 and the ultrasound device 33 are attached to the patient support plate 7 of the patient support table 1 so that they do not impede the motion and action space of the operating team working at the system workstation and also do not have a disturbing influence.

The cold light source 13, the RF device 14, the video device 15 and the ultrasound device 33, given a corresponding embodiment of the patient support plate 7, can also be arranged in the patient support plate 7 or, given corresponding implementation of the lifting column 6, can be arranged in the lifting column of the patient support table 1.

FIGS. 2 through 6 show further embodiments of the inventive system workstation, wherein components of the system workstations of FIGS. 2 through 6 that are substantially structurally and functionally the same as components of the system workstation of FIG. 1 are provided with the same reference numerals.

Figure 2:
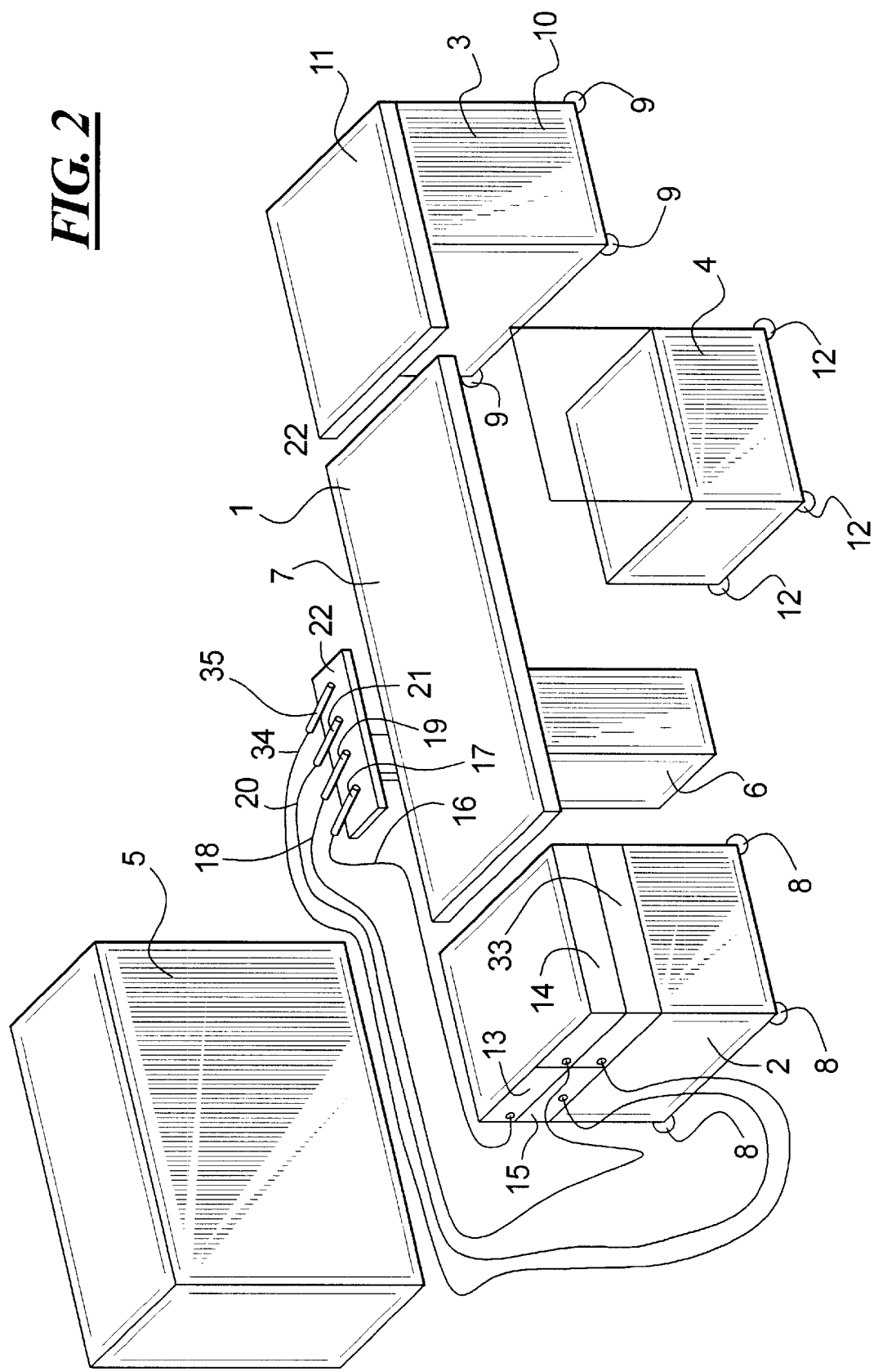
FIG. 2 shows an inventive system workstation, wherein a cold light source, a RF device, a video device and an ultrasound device are arranged in an anesthesia tower.

In the system workstation shown in FIG. 2, the cold light source 13, the RF device 14, the video device 15 and the ultrasound device 33 are integrated in the anesthesia tower 2 of the system workstation. The cold light 17 is again connected via a connecting line 16 to the cold light source 13; the high-frequency scalpel 19 is connected to the RF device 14 via a connecting line 18; the endoscope camera 21 is connected to the video device 15 via a connecting line 20; and the ultrasound device 33 is connected to the ultrasound applicator 35 via a connecting line 34. The cold light 17, the high-frequency scalpel 19, the endoscope camera 21 and the ultrasound applicator 35 are again placed on a presentation unit 22 that is arranged at the patient support plate 7 of the patient support table 1. As in the exemplary embodiment described above, the connecting lines 16, 18, 20, 34 are significantly shorter than the connecting lines of the devices arranged in the device cabinet 5, whose applicators can likewise be placed on the presentation unit 22 in a way that is not shown. The cold light source 13, the RF device 14, the video device 15 and the ultrasound device 33 are advantageously arranged in a unit that is already disposed in the immediate proximity of the patient support table 1 given a surgical procedure, so that the motion and action space of the operating team is not impeded by a close arrangement of the cold light source 13, of the RF device 14, of the video device 15 and of the ultrasound device 33 at the patient support table 1.

Figure 3:
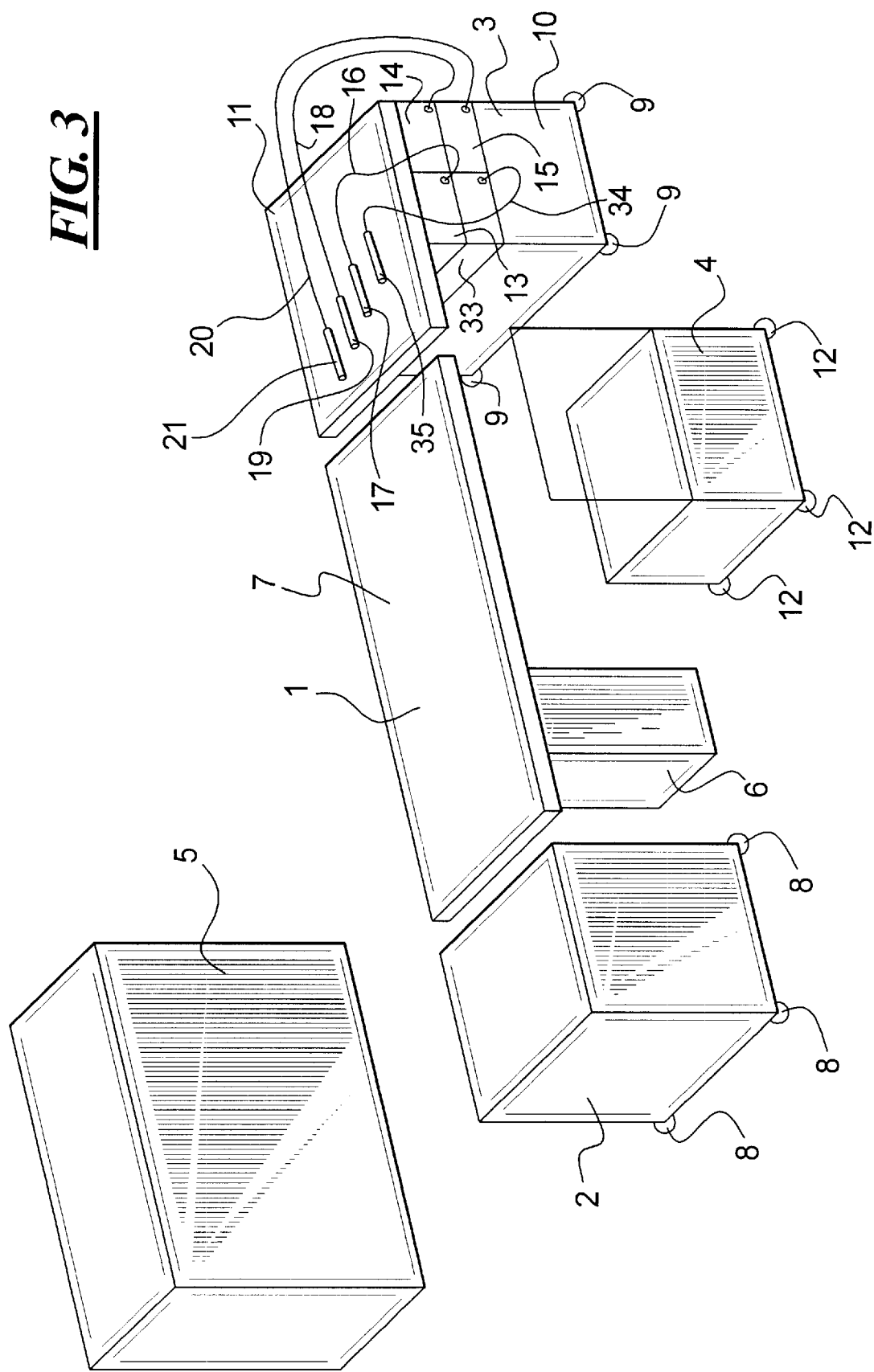
FIG. 3 shows an inventive system workstation, wherein a cold light source, a RF device, a video device and an ultrasound device are arranged in an instrumentation table.

FIG. 3 shows a third embodiment of the inventive system workstation, wherein the cold light source 13, the RF device 14, the video device 15 and the ultrasound device 33 are arranged in the instrumentation table 3 of the system workstation. As in the exemplary embodiments described earlier, the cold light 27, the high-frequency scalpel 19, the endoscope camera 21 and the ultrasound applicator 35 are connected via connecting lines 16, 18, 20, 34 to the cold light source 13, the RF device 14, the video device 15, and to the ultrasound device 33, respectively. Differing from the exemplary embodiments described before, the cold light 17, the high-frequency scalpel 19, the endoscope camera 21 and the ultrasound applicator 35 are not arranged on a presentation unit but rather on the table top 11 of the instrumentation table 3. In this exemplary embodiment too, the connecting lines 16,18, 20, 34 are kept short, so that no problems occur in the signal transmission. Since the instrumentation table 3 that accepts the cold light source 13, the RF device 14, the video device 15 and the ultrasound device 33 is already arranged at the patient support table 1 given a surgical procedure, the motion and action space of the operating team is likewise not impeded by such an arrangement of the cold light source 13, the RF device 14, the video device 15 and the ultrasound device 33.

Figure 4:
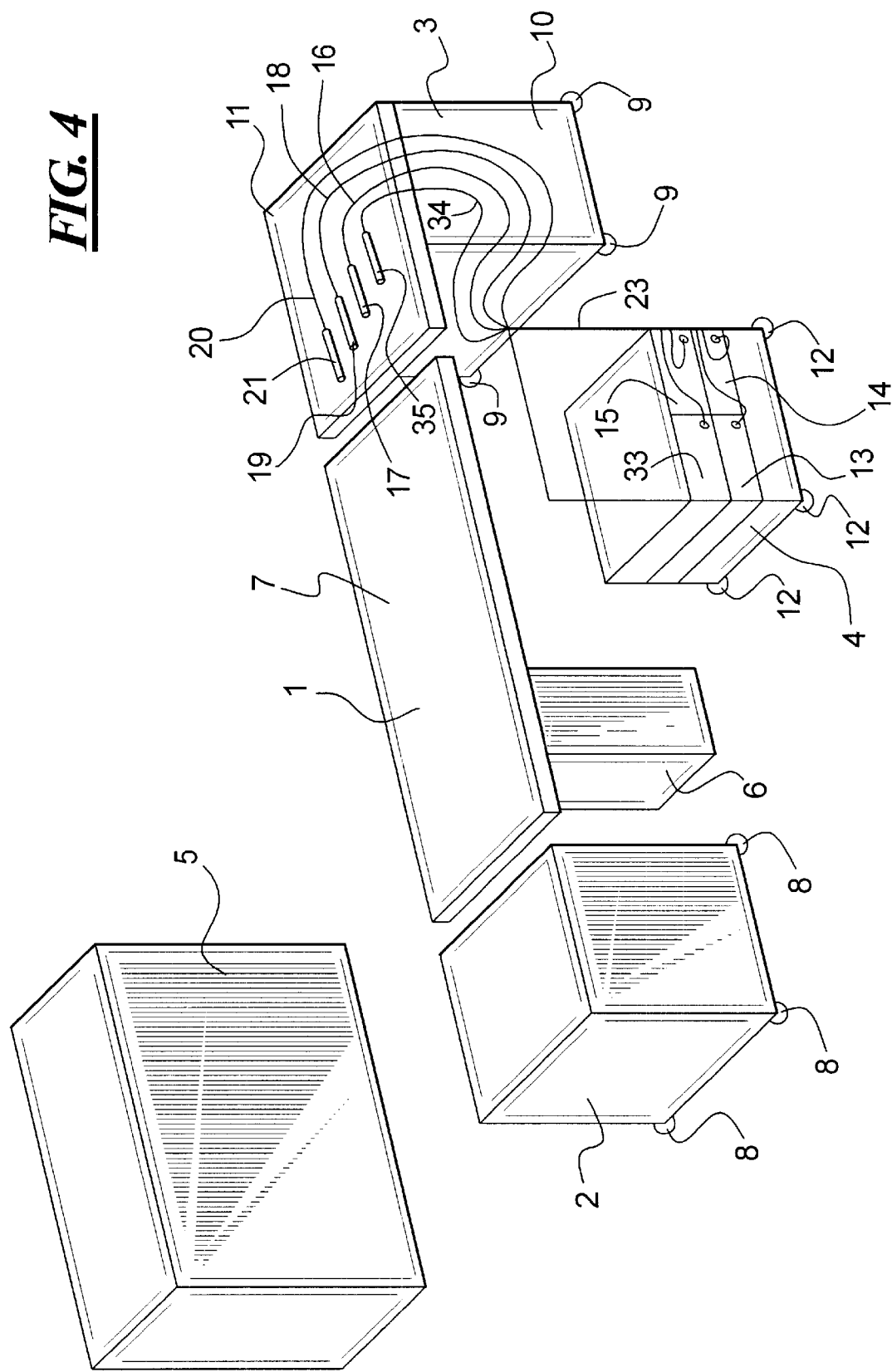
FIG. 4 shows an inventive system workstation, wherein a cold light source, a RF device, a video device and an ultrasound device are arranged in an operating seat.

In a fourth embodiment of the inventive system workstation shown in FIG. 4 the cold light source 13, the RF device 14, the video device 15 and the ultrasound device 33 are arranged in the operating seat 4 of the system workstation. In this exemplary embodiment, the connecting lines 16,18, 20, 34 are conducted via a structural element 23 of the operating seat 4 to the applicators placed on the table top 11 of the instrumentation table 3, namely the cold light 17, the high-frequency scalpel 19, the endoscope camera 21 and the ultrasound applicator 35. These are thus ready on the table top 11 for an operating team working at the system workstation. As in the exemplary embodiments described earlier, the arrangement of the cold light source 13, the RF device 14, the video device 15 and the ultrasound device 33 in the operating seat 4, which is already arranged at the patient bearing table 1 given surgical interventions, has the advantage that no additional space requirement around the patient bearing table 1 is necessary for the immediate arrangement of the cold light source 13, the RF device 14, the video device 15 and the ultrasound device 33 at the patient support table 1. Given short connecting lines 16, 18, 20, 34 between the devices 13, 14, 15, 33 and the appertaining applicators 17, 19, 21, 35, the movement and action space for an operating team is not impeded around the patient support table 1 in this way.

Figure 5:
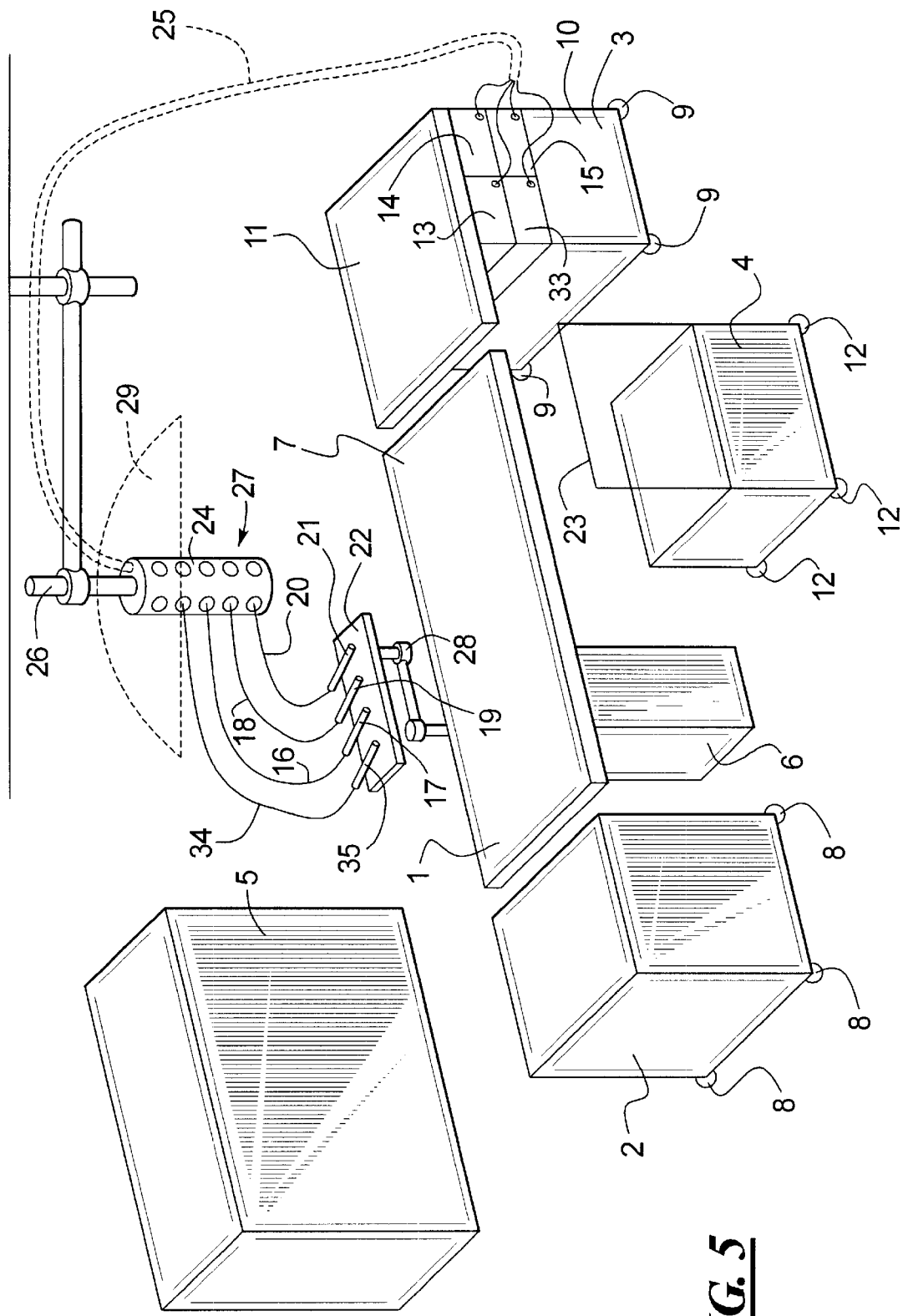
FIG. 5 shows an inventive system workstation with a connection unit for applicators of medical devices.

Compared to the exemplary embodiments shown in FIGS. 1 through 4, in the exemplary embodiment of the system workstation shown in FIG. 5, a connection unit 24 for the applicators of the medical devices is provided. The cold light source 13, the RF device 14, the video device 15 and the ultrasound device 33, which are arranged in the instrumentation table 3 in the exemplary embodiment, are connected to the connection unit 24 via a line 25 (only schematically indicated) that accepts the connecting lines of the devices. The connection unit 24 is arranged at a vertically and horizontally adjustable holder in the form of a ceiling-mounted articulated arm 26 and is provided with a number of connectors 27 for cold lights, high-frequency applicators, cameras and ultrasound applicators that are connected to the corresponding devices. In the exemplary embodiment, the cold light 17 is connected to the connecting line 16, the high-frequency scalpel 19 is connected to the connecting line 18, the endoscope camera 21 is connected to the connecting line 20 and the ultrasound applicator is connected to the connecting line 34 at four matching connectors 27 of the connection unit 24. The cold light 17, the high-frequency scalpel 19, the endoscope camera 21 and the ultrasound applicator 35 are arranged on the presentation unit 22. Differing from the above-described exemplary embodiments, the presentation unit 22 is arranged at a vertically and horizontally adjustable articulated arm 28 secured to the patient support plate 7.

The employment of the connection unit 24 for the connection of the applicators of the of the cold light source 13, the RF device 14, the video device 15 and the ultrasound device 35 has the advantage that the path for the cable of the connecting lines 18, 19, 20, 34 of the cold light 17, the high-frequency scalpel 29, the endoscope camera 21 and the ultrasound applicator 35 is practically parallel from the connection unit 24 to the presentation unit 22, resulting in a simple cable management at the system workstation derives. Due to the arrangement of the connection unit 24 at the adjustable articulated arm 26, the connection unit 24 can also be aligned relative to the patient bearing table 1 or relative to the patient as desired and according to the operating situation, allowing the path of the cable from the connection unit 24 to the medical applicators to be selected by the operating team. The presentation unit 22 can likewise be aligned relative to the patient with the articulated arm 28 and thus can be adapted to the respective operation situation.

In a further embodiment of the system workstation, the connection unit 24 can also be integrated in an operating lamp 29 that is schematically indicated in FIG. 5. In this way, the connection unit 24—given a surgical intervention—can be adjusted relative to the patient, or relative to the operating site together with the operating lamp 29. A synergistic effect is achieved so that, with an alignment of the operating lamp 29, the operating lamp 29 itself as well as the connection unit 24 are suitably aligned relative to the patient.

Figure 6:
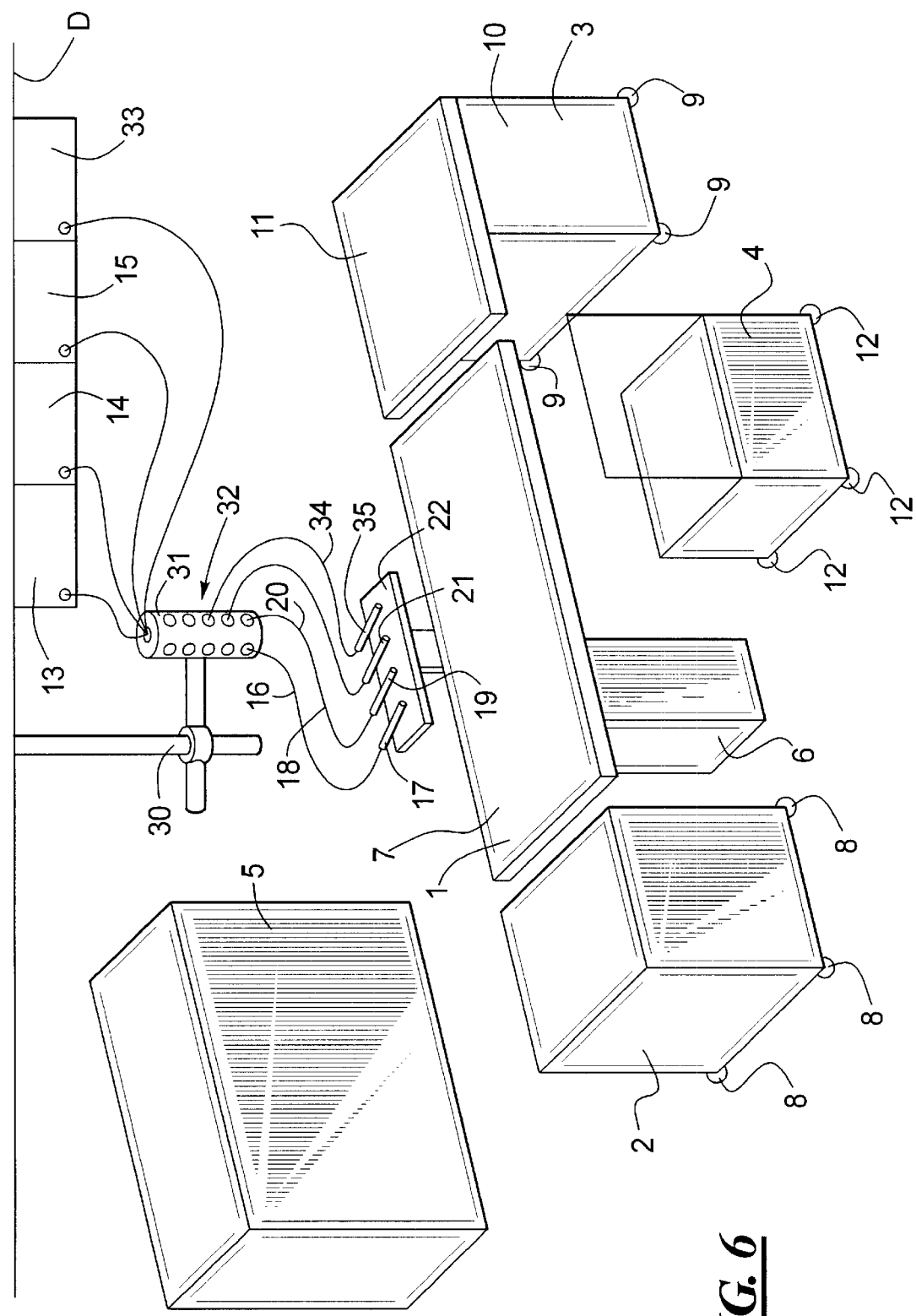
FIG. 6 shows an inventive system workstation, wherein a cold light source, a RF device, a video device and an ultrasound device are arranged at the ceiling of a room accepting the workstation.

FIG. 6 shows a further embodiment of the inventive system workstation, wherein the cold light source 13, the RF device 14, the video device 15 and the ultrasound device 33 are attached to the ceiling D of the room accepting the system workstation. In the exemplary embodiment, the cold light source 13, the RF device 14, the video device 15 and the ultrasound device 33 are attached in the ceiling region above the patient support table 1. The cold light source 13, the RF device 14, the video device 15 and the ultrasound device 33—via connecting lines that are not shown in greater detail—are connected to a connection unit 31 arranged at a ceiling-mounted, adjustable articulated arm 30. The connection unit 31, like the connection unit 24, is provided with a number of connectors for cold lights, high-frequency applicators, cameras and ultrasound applicators. As in the exemplary embodiment shown in FIG. 5, the cold light 17, the high-frequency scalpel 19, the endoscope camera 21, and the ultrasound applicator 35 are connected by connecting lines 16, 18, 20, 34 to matching connectors 32 of the connection unit 21. The applicators 17, 19, 21, 35 are arranged ready to be grasped by an operating team on the presentation unit 22.

The arrangement of cold light sources, RF devices, video devices and the ultrasound devices at ceiling of a treatment room also enables short connecting lines between the devices and the appertaining applicators, so that problems in the signal transmission due to line losses, noise levels and impedance discontinuities can be avoided. A connection unit 31 need not necessarily be present; rather, the applicators 17, 19, 21, 24 alternatively can be directly connected to the devices 13, 14, 15, 33 with connecting lines.

The cold light source 13, the RF device 14, the video device 15 and the ultrasound device 33, moreover, need not necessarily all be arranged at the ceiling D, or in a single unit, for example in the operating seat 4, but can also be arranged in different units, for example the cold light source 13 in the anesthesia tower 2, the RF device 14 and the instrumentation table 3 and the video device 15 and the ultrasound device 33 in the operating seat 4.

Further, more than one of these devices can also be attached to the ceiling D or in or at the patient support table 1 or in or at the anesthesia tower 2, the instrumentation table 3 or the operating seat 4.

The system workstation, however, need not necessarily include devices of the categories of cold light source, RF device, video device and ultrasound device but can instead include only one, two or three categories of devices.

The inventive system workstation, moreover, need not necessarily have an anesthesia tower 2, an instrumentation table 3 and an operating seat 4 available to it; on the contrary, only an anesthesia tower 2 or an instrumentation table 3 or an operating seat 4 can be present, the cold light source 13, the RF device 14, the video device 15 or the ultrasound device 33 being attached therein or thereat.

Further, further applicators of medical devices can also be arranged on the presentation unit 22.

The presentation unit 22 need not necessarily be arranged at the patient support plate 7 of the patient support table 1 but, for example, can be arranged at the anesthesia tower 2, the instrumentation table 3 or somewhere else.

The anesthesia tower 2 and the instrumentation table 3, moreover, just like the operating seat 4, can have a correspondingly implemented structural part for guiding lines therein.

The connection units 24, 31 need not be arranged at a ceiling-mounted articulated arm but, for example, can be arranged at a floor-mounted or wall-mounted, adjustable holder, for example, a goose neck.

Although modifications and changes may be suggested by those skilled in the art, it is the intention of the inventors to embody within the patent warranted hereon all changes and modifications as reasonably and properly come within the scope of their contribution to the art.

What is claimed is:

1. A medical-technical system workstation for conducting a surgical procedure, comprising:

a patient support mechanism;

multiple medical devices for use in open or minimally invasive surgery selected from the group consisting of a cold light source, an RF device, a video device, and an ultrasound device, each of said multiple medical devices having at least one applicator connected thereto;

a movable anesthesia tower adapted for placement adjacent to said patient support mechanism; and said multiple medical devices being disposed at a location selected from the group of locations consisting of a ceiling of a room containing said workstation, said patient support mechanism, and said movable anesthesia tower.

2. A medical-technical system workstation as claimed in claim 1 wherein said multiple medical devices is a cold light source and wherein said at least one applicator is a cold light applicator.

3. A medical-technical system workstation as claimed in claim 1 wherein said multiple medical devices is an RF device, and wherein said at least one applicator is a high-frequency scalpel.

4. A medical-technical system workstation as claimed in claim 1 wherein said multiple medical devices is a video device, and wherein said at least one applicator is a video camera.

5. A medical-technical system workstation as claimed in claim 1 wherein said multiple medical devices is an ultrasound device, and wherein said at least one applicator is an ultrasound applicator.

* * * * *